US012653989B2

(12) United States Patent
Kastelein et al.

(10) Patent No.: US 12,653,989 B2
(45) Date of Patent: Jun. 16, 2026

(54) METHOD FOR MANUFACTURING A MAGNET AND SYSTEMS AND DEVICES INCLUDING A MAGNET

(71) Applicant: Stereotaxis, Inc., St. Louis, MO (US)

(72) Inventors: Nathan Kastelein, Troy, IL (US); Paul F. Rebillot, III, St. Louis, MO (US); Wilfred Peter Heiner, Rheinfelden (DE)

(73) Assignee: Stereotaxis, Inc., St. Louis, MO (US)

( * ) Notice: Subject to any disclaimer, the term of this patent is extended or adjusted under 35 U.S.C. 154(b) by 790 days.

(21) Appl. No.: 17/900,916

(22) Filed: Sep. 1, 2022

(65) Prior Publication Data

US 2023/0071158 A1     Mar. 9, 2023

Related U.S. Application Data

(60) Provisional application No. 63/239,499, filed on Sep. 1, 2021.

(51) Int. Cl.
*H01F 7/06* (2006.01)
*A61M 25/00* (2006.01)
(Continued)

(52) U.S. Cl.
CPC .... *A61M 25/0158* (2013.01); *A61M 25/0013* (2013.01); *A61M 25/0138* (2013.01);
(Continued)

(58) Field of Classification Search
CPC .......... A61M 25/0009; A61M 25/0013; A61M 25/0127; A61M 25/0138; A61M 25/0158;
(Continued)

(56) References Cited

U.S. PATENT DOCUMENTS

| | | | |
|---|---|---|---|
| 5,385,578 A | 1/1995 | Bush et al. | |
| 7,335,317 B2 * | 2/2008 | Hong | H10N 35/85 335/215 |

(Continued)

FOREIGN PATENT DOCUMENTS

| | | |
|---|---|---|
| DE | 832734 C | 2/1952 |
| GB | 191319234 A | 2/1914 |

(Continued)

OTHER PUBLICATIONS

DFT® wire web page; https://www.fwmetals.com/services/resource-library/dft-wire/, 2022, 3 pages.

(Continued)

*Primary Examiner* — Paul D Kim
(74) *Attorney, Agent, or Firm* — Cooley LLP

(57) ABSTRACT

Methods described herein can include drawing materials to form a drawn filled tubing (DFT) wire. The materials can include a core material, a first layer of a biocompatible material disposed exterior to the filler material, a magnetic material disposed external to the first layer of biocompatible material, and a second layer of biocompatible material disposed exterior to the magnetic material. In some embodiments, the method further comprises melting the core material to form a magnet with a through hole lumen. In some embodiments, the method can further include applying an external magnetic field to the materials during the drawing to align grains of the magnetic material. In some embodiments, the core material can have a melting point lower than a melting point of the magnetic material and the biocompatible material.

18 Claims, 12 Drawing Sheets

(51) Int. Cl.

| | |
|---|---|
| *A61M 25/01* | (2006.01) |
| *B21C 1/02* | (2006.01) |
| *H01F 41/02* | (2006.01) |
| *C22F 1/04* | (2006.01) |
| *C22F 1/14* | (2006.01) |
| *H01F 7/02* | (2006.01) |

(52) U.S. Cl.
CPC ........... *B21C 1/02* (2013.01); *H01F 41/0253* (2013.01); *C22F 1/04* (2013.01); *C22F 1/14* (2013.01); *H01F 7/0215* (2013.01)

(58) Field of Classification Search
CPC ............... A61B 34/73; A61B 18/1492; A61B 2018/00577; B21C 1/02; B21C 37/042; B21C 37/045; B21C 37/047; B21C 37/154; B21C 1/003; H01F 41/0253; H01F 41/0273; H01F 7/0215; C22F 1/04; C22F 1/14; B21L 11/005
See application file for complete search history.

(56) References Cited

U.S. PATENT DOCUMENTS

| | | | |
|---|---|---|---|
| 7,420,124 B2 | 9/2008 | Michael et al. | |
| 7,745,732 B2 * | 6/2010 | Michael | A61N 1/056 |
| | | | 174/128.1 |
| 8,632,532 B2 | 1/2014 | Phan et al. | |
| 9,084,877 B2 | 7/2015 | Levy et al. | |
| 9,918,705 B2 | 3/2018 | Giles | |
| 9,987,130 B2 | 6/2018 | Weber | |
| 10,926,068 B2 | 2/2021 | Narayan et al. | |
| 10,994,109 B2 | 5/2021 | Hakim et al. | |
| 2003/0032997 A1 * | 2/2003 | Pianca | A61N 1/0534 |
| | | | 607/117 |
| 2009/0043246 A1 | 2/2009 | Dominguez | |
| 2009/0241598 A1 | 10/2009 | Solanilla | |
| 2016/0093426 A1 | 3/2016 | Yoshida et al. | |
| 2021/0134491 A1 | 5/2021 | Nakamura et al. | |

FOREIGN PATENT DOCUMENTS

| | | |
|---|---|---|
| JP | H01171215 A | 7/1989 |
| JP | H01261806 A | 10/1989 |
| WO | WO-2023034887 A1 | 3/2023 |

OTHER PUBLICATIONS

International Search Report and Written Opinion for International Application No. PCT/US2022/075799 dated Jan. 3, 2023, 15 pages.
International Preliminary Report on Patentability for International Application No. PCT/US2022/075799 dated Mar. 14, 2024, 10 pages.
Office Action for European Application No. 22777164.9, dated Mar. 11, 2025, 4 pages.

* cited by examiner

FIG. 1

Magnetic Device
100

Proximal Handle
102

Catheter
120

Magnet(s)
110

400

Arrange different materials around core material
410

Draw material to form DFT wire
401

Apply external magnetic field during or after drawing
402

Anneal drawn material
403

Melt core material to form DFT magnet
404

Cut DFT magnet into desired shape
405

Construct medical device (e.g., catheter) with DFT magnet(s)
406

METHOD FOR MANUFACTURING A MAGNET AND SYSTEMS AND DEVICES INCLUDING A MAGNET

CROSS REFERENCE TO RELATED APPLICATIONS

This application claims the benefit of U.S. Provisional Application No. 63/239,499, titled, "Magnetic Devices Constructed from Drawn Tube Magnets," and filed Sep. 1, 2021, the content of which is incorporated herein by reference in its entirety.

TECHNICAL FIELD

Embodiments described herein generally relate to magnetic devices and more specifically to systems and devices including drawn filled tubing (DFT) magnets and methods of producing the same.

BACKGROUND

Interventional or surgical procedures can involve navigation of catheters and other medical devices through a vessel, lumen, or other space within patient anatomy. For example, catheterization is a common practice for electrophysiology mapping, ablation, and/or other medical procedures. During catheterization, thin, flexible tubes with sensing and/or treatment elements can enter the vasculature of the patient and be guided to a target site (e.g., a cardiac chamber of a heart). In many applications, magnetic fields can be used to steer the tip of a catheter or other medical device. In such applications, the tip of the catheter or other device can include one or more magnets that are steered using externally applied magnetic fields.

The production of magnets used in guidewires, catheters, and other medical devices for magnetically guided navigation can be difficult as such devices are built to smaller dimensions. Traditional methods of manufacturing small magnets are reaching practical limits. In many applications, magnets require an open hole through the center of the magnet, which can complicate the construction of such magnets. Current manufacturing processes for small magnets, such as neodymium iron boron (NdFeB) magnets and the material properties of these magnets make creating these types of small through-hole magnets difficult and expensive. Magnets made using traditional methods are also rigid in nature, and therefore, with many applications requiring more flexible devices, need to be limited to shorter dimensions and separated by more flexible portions of the device. There also exists a physical limit to how small such magnets can be made with current manufacturing processes. It is therefore desirable to have more robust methods of manufacturing small magnets.

SUMMARY

Embodiments described herein relate to magnets and magnetic devices constructed from DFT processes, and methods relating to the same. In an example embodiment, methods described herein can include drawing material to form a drawn filled tubing wire. The material being drawn can include several concentric layers or sections or layers. For example, the material can include a core or filler material, a first layer of a biocompatible material disposed around the core material, a magnetic material disposed around the first layer of biocompatible material, and a second layer of biocompatible material disposed around the magnetic material. The method further comprises melting the core material after drawing the material, leaving the layers of biocompatible material and the magnetic material which together form a magnet with a through hole lumen. In some embodiments, the method can further include applying an external magnetic field to the material during or after the drawing process to align grains of the magnetic material. In some embodiments, the filler material can include silver, which has a lower melting point than the biocompatible material and the magnetic material. In some embodiments, the magnetic material can include NdFeB, iron platinum (FePt), cobalt platinum (CoPt), iron nitrodes ($Fe_xN$) or ferroniobium (FeNb). In some embodiments, the method can further include annealing the material to improve ductility of the drawn filled tubing wire. In some embodiments, the method can further include cutting (e.g., laser cutting) the magnet to form a series of patterns on the magnet to add flexibility to the magnet.

BRIEF DESCRIPTION OF THE DRAWINGS

FIG. 1 is a block diagram of an example DFT magnetic device, according to an embodiment.

FIGS. 6A-6C illustrate components and assemblies of devices including DFT magnets, according to various embodiments.

DETAILED DESCRIPTION

Embodiments described herein relate to DFT magnets and methods of producing the same. Depending on the application, DFT magnets can be constructed to include a through-hole lumen, such that the DFT magnets can be placed around a catheter shaft, guidewire, or other medical components (e.g., a lead wire, a heating wire, etc.) and/or allow delivery of fluids or agents via the lumen. In some embodiments, DFT magnets constructed using methods described herein can be flexible, such that longer magnets can be used without sacrificing the flexibility needed in many medical applications (e.g., for navigating through tortuous anatomy). Existing magnetic devices include small magnets that are rigid. Small through holes can be formed in the magnets by drilling through a solid magnet. This drilling process is expensive, energy intensive, and requires great precision to execute properly, especially with smaller dimensions. A drawn wire technique can enable construction of small magnets with various inner and outer diameters, and of varying lengths, with greater precision and efficiency than conventional methods.

Using a DFT wire drawing technique, a tube with inner and outer layers made of biocompatible materials can be made with a layer between the inner and outer layers filled with magnetizable materials. To form the tube, a DFT wire can be constructed with a central core, the inner and outer tube layers, and the magnetizable layer disposed between the inner and outer tube layers. The DFT wire can be drawn using tube drawing processes such as, for example, sinking, rod drawing, or floating, fixed, or tethered plug drawing. The central core of the DFT wire can be made from a metal with a lower melting point than the other layers of the DFT wire (e.g., the inner and outer layers of biocompatible materials and the magnetizable material between the inner and outer layers of biocompatible materials). As such, after the DFT wire is drawn using a tube drawing process, the central core can be melted out, leaving a hollow void. The resulting structure can be a single tubular magnet with a through-lumen in place of the melted out core, thus eliminating a need to drill holes in the magnets. In some embodiments, the DFT wire can be drawn to any desired diameter, and magnets of any desired length can be cut from the wire. This enables the production of magnets or micromagnets of varying diameters and length.

Figures 5A, 5B, 5C:
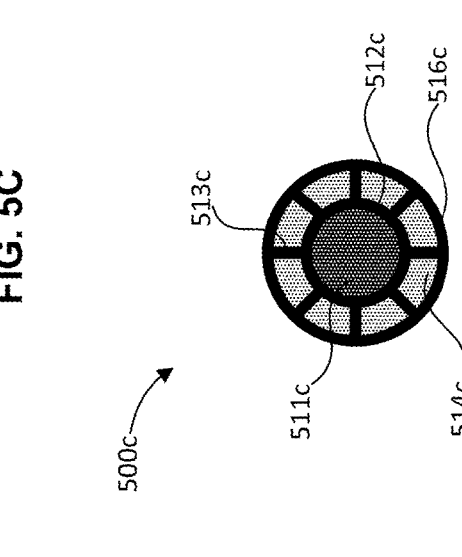
FIGS. 5A-5C are illustrations of cross-sections of DFT magnets during construction with core materials disposed therein, according to various embodiments.

In some embodiments, the inner and outer layers can provide resistance to corrosion in addition to their biocompatible properties. Additionally, the layers of the DFT wire can be organized into sections. In other words, the DFT wire can include multiple sections, such that when the wire is drawn, one or more supports can form between the inner and outer layers. FIGS. 5A-5C, described below, provide a more detailed description of DFT wires with multiple sections.

Magnets with a tubular configuration can greatly simplify the process of producing magnetically enabled medical devices. For example, such magnets can be mounted on a tapered wire core to provide a multiple magnet guidewire with significantly improved navigation capabilities over traditional magnetic guidewire production using solid magnets. Tubular magnets can be made of an appropriate size for use in microcatheters, guide catheters, ablation catheters, and other navigation and/or therapeutic catheters. Tubular magnets can simplify the construction process of such medical devices and allow the magnet to be incorporated into the tubular structure of these devices.

Tubular magnets can be made in longer sections than other magnet designs. Through cutting (e.g., laser cutting) of channels and/or slots into the tubular magnet, the tubular magnet can have a range of flexibility and shaping characteristics. Longer tubular magnets can include laser cut slots for flexibility. With the tubular magnets being flexible and therefore not requiring non-magnetic portions to provide flexibility, greater density of magnetic material can be used near the end of a device without significantly sacrificing bending performance. Laser cuts can be designed to give a medical device various shapes in response to an externally applied magnetic field, thus allowing the device to be tailored to specific medical applications with simple changes in the laser cutting pattern. This can make the overall production process of such devices simpler and reduce the cost of magnetically operated medical devices. Laser cut tubular magnets can be made in a range of diameters from very small guidewire sizes up to much larger endoscopic size devices.

In some embodiments, tubular magnets as described herein can be cut (e.g., laser cut) to have a tab-in-slot pattern or configuration. Laser cutting patterns that create a tab-in-slot type configuration can allow brittle and stiff materials such as NdFeB or FeNb to gain flexibility. This technique allows a stiff magnetic element to flex without requiring the addition of flexible materials in between stiff magnets, as is traditionally done in magnetic devices. With the traditional approach, the magnets are rigid and therefore require separation by sufficient flexible material to allow the device to curve or bend appropriately, which spreads out the magnetic material and reduces the magnetic flux. This can be avoided in a tubular laser cut magnet, which can allow the magnetic material to be concentrated without the need for flexible material to allow bending.

Figure 1:
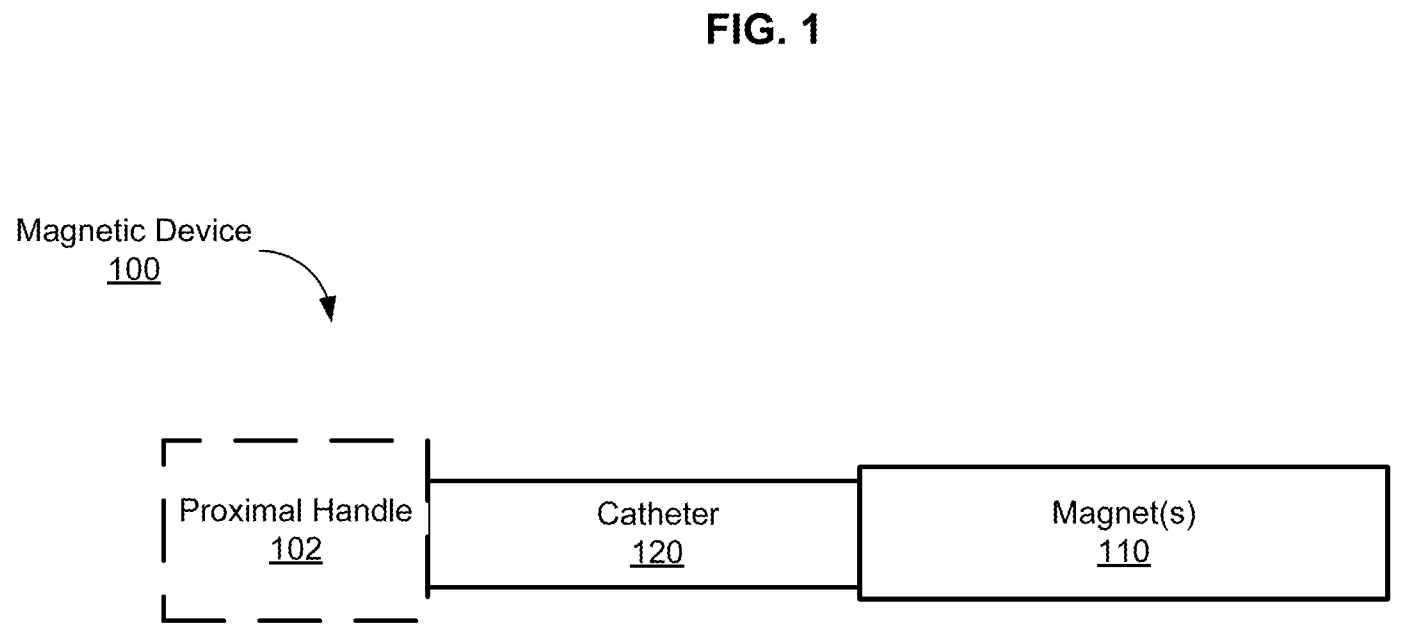

FIG. 1 is a block diagram of a magnetic device 100 produced using a DFT process, according to an embodiment. As shown, the magnetic device 100 includes magnet(s) 110 that can be disposed on a distal portion of a catheter 120 (or other elongate structure, e.g., a guide wire, a shaft, etc.). In some embodiments, the magnetic device 100 can be steerable via a magnetic field, such that the device 100 can be precisely guided through a body lumen. Magnetically steerable catheters are described in greater detail in U.S. Provisional Patent Application No. 63/238,304 ("the '304 application"), filed Aug. 30, 2021, entitled "Magnetically Steerable Irrigated Ablation Catheter," the disclosure of which is hereby incorporated by reference in its entirety.

The magnet(s) 110 can be formed from a DFT process. In other words, the magnet(s) 110 can be formed by drawing multiple materials into single wire and then cutting the wire to form individual magnets. In some embodiments, the magnet(s) 110 can be tubular, i.e., have a through-lumen, where a core of the wire can be removed (e.g., melted out) after forming the DFT wire. In some embodiments, the magnet(s) 110 can include iron, nickel, cobalt, neodymium, boron, rare earth metals, aluminum, NdFeB, FeNb, FePt, CoPt, $Fe_xN$, alnico, permalloy, and any other suitable magnetic material, or combinations thereof. In some embodiments, the magnet(s) 110 can be composed of a magnetic material, a ferromagnetic material, or any combination thereof. In some embodiments, the magnet(s) 110 can have an outer layer that is formed of a biocompatible material. In some embodiments, the magnet(s) 110 can have an inner layer that is formed of a biocompatible material. In some embodiments, the magnet(s) 110 can include multiple inner and/or outer biocompatible layers or coatings (e.g., an additional coating), e.g., for protection. In some embodiments, the magnet(s) 110 can be coated by a polymer such as, for example, parylene. In some embodiments, the magnetic device 100 can include ferromagnetic elements (not shown) placed in contact with or integrated with one or more of the magnets 110. In some embodiments, the ferromagnetic elements can enhance the magnetic effects of the magnets 110.

In some embodiments, the magnetic device 100 can include at least about 1 magnet 110 and up to about 100 magnets 110, inclusive of all values and ranges therebetween.

In some embodiments, the magnetic device 100 can include a single magnet 110 (or lesser number of magnets 110) that is longer in length and provides magnetic flux that is greater than or comparable to a plurality of magnets 110. In some embodiments, one or more magnet(s) 110 can be flexible, e.g., have laser cut slots that enable the magnet 110 to curve or flex. In some embodiments, the magnet(s) 110 can be configured to curve smoothly, i.e., without any discontinuities and/or sharp bends. In some embodiments, the magnet(s) 110 can have sections that curve about different axes (i.e., have a plurality of concave or convex curves). In some embodiments, the magnet(s) 110 can take on a compound curve shape.

In some embodiments, the catheter 120 can be flush or substantially flush with the magnet(s) 110, such that the magnet(s) 110 do not increase a cross-sectional profile of the catheter 120. Alternatively, in some embodiments, the magnet(s) 110 can be placed over a shaft of the catheter 120, thereby increasing the diameter of the shaft 120 in the areas where the magnet(s) 110 are located. In some embodiments, a longer, flexible magnet 110 can form an entire section of the catheter 120, e.g., a distal portion of the catheter 120, without requiring any flexible material of the catheter 120 to provide flexibility. In some embodiments, the catheter 120 can include a polymer, an elastomer, a polyamide, Zytel®, Rilsan®, Grilamid®, Vestamid®, Pebax®, polyethylene terephthalate (PETE), polytetrafluoroethylene (PTFE), poly-vinyl chloride (PVD), polyethylene (PE), polypropylene (PP), polystyrene (PS), or any other suitable material or combinations thereof. In some embodiments, the catheter 120 can have a diameter of about 3 Fr, about 3.5 Fr, about 4 Fr, about 4.5 Fr, about 5 Fr, about 5.5 Fr, about 6 Fr, about 6.5 Fr, about 7 Fr, about 7.5 Fr, about 8 Fr, about 8.5 Fr, about 9 Fr, about 9.5 Fr, or about 10 Fr, inclusive of all values and ranges therebetween. In some embodiments, the catheter 120 can be a single use catheter. In some embodiments, the catheter 120 can be a reusable catheter.

In some embodiments, the magnetic device 100 can include electrodes, sensors, and/or other sensing and/or treating elements (not shown) disposed on the catheter 120. For example, the catheter 120 can include ring electrodes disposed around the catheter 120, a tip electrode disposed at the tip of the catheter 120 and/or magnet 110, sensor(s) disposed throughout a length of the catheter and/or magnet, etc. Further examples of electrodes and sensors that can be disposed on a catheter are described in the '304 application.

Figure 2B:
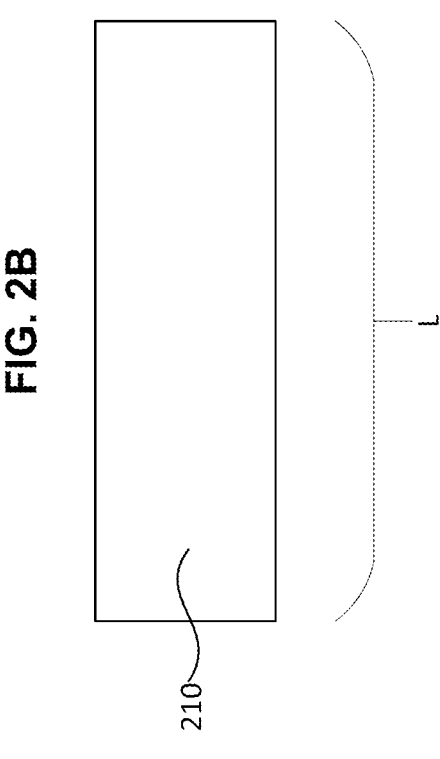
FIGS. 2A-2C are schematic illustrations of a DFT magnet, according to an embodiment.
Figure 2A:
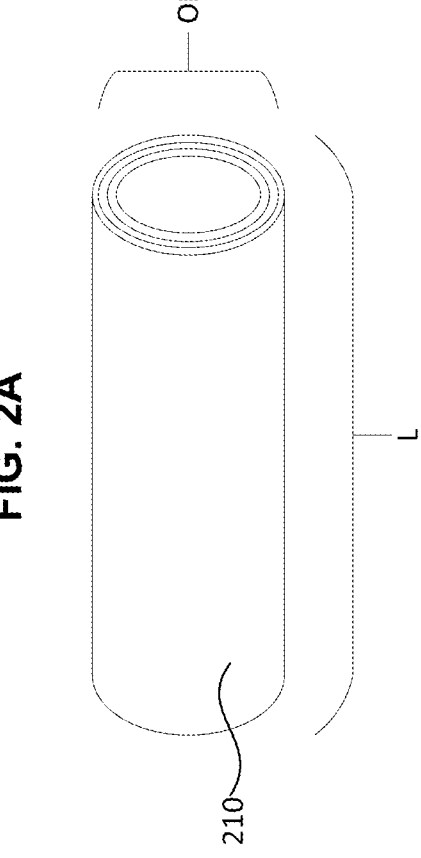
Figure 2C:
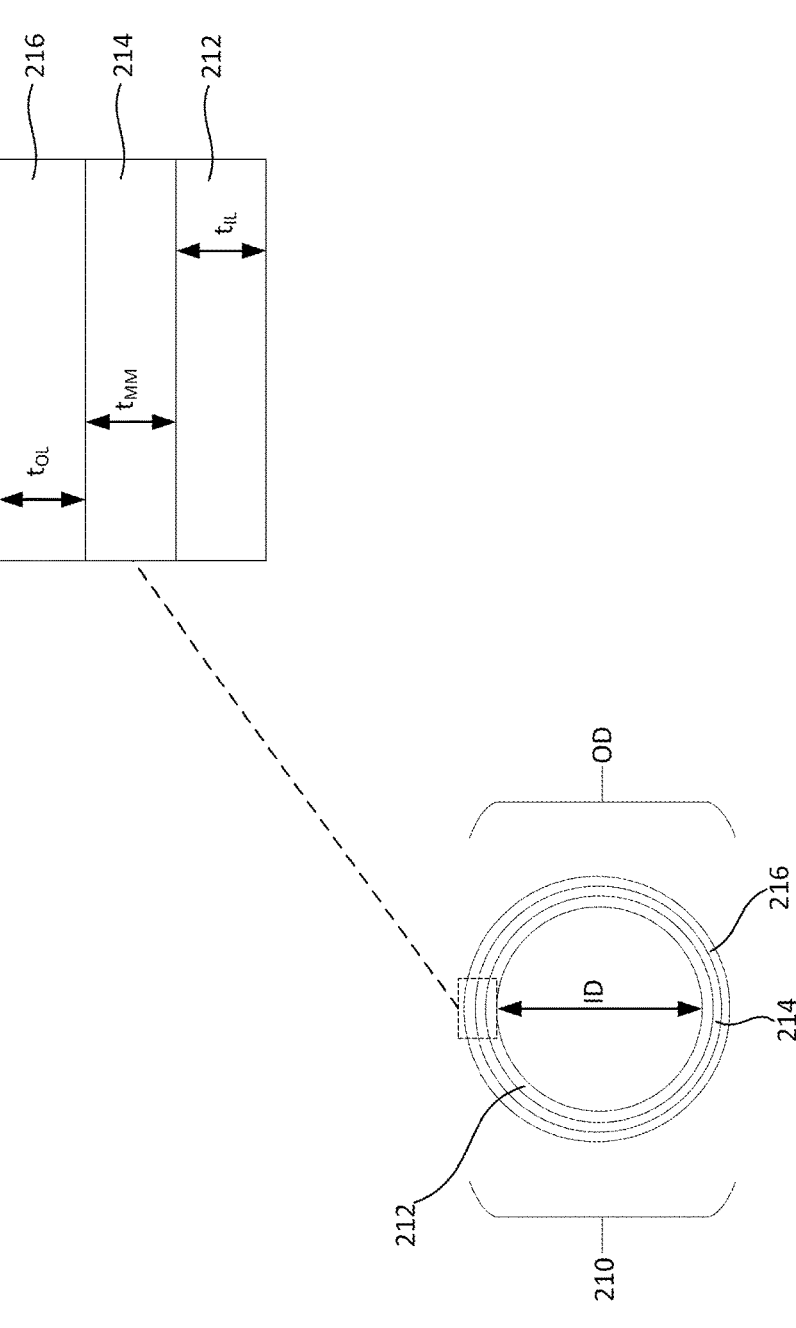

FIGS. 2A-2C provide detailed views of a magnet 210 formed from a DFT process, according to an embodiment. FIG. 2A shows an auxiliary view of the magnet 210, while FIG. 2B shows a side cross-sectional view of the magnet 210 and FIG. 2C shows a front view or axial cross-sectional view of the magnet 210. In some embodiments, the magnet 210 can be the same or substantially similar to the magnet(s) 110, as described above with reference to FIG. 1. Thus, certain aspects of the magnet 210 are not described in greater detail herein. As shown, the magnet 210 includes an inner layer 212, a magnetic layer 214, and an outer layer 216.

The magnet 210 has a length L, an outer diameter OD, and an inner diameter ID. In some embodiments, the length L can be at least about 200 μm and up to about 5 cm, inclusive of all values and ranges therebetween. In some embodiments, the outer diameter OD can be at least about 50 μm, and up to about 1 cm, inclusive of all values and ranges therebetween.

In some embodiments, the inner diameter ID corresponds to a diameter of a through-lumen of the magnet 210. In some embodiments, this through-lumen can be sized to receive a shaft of a catheter (e.g., the catheter 120) or a wire (e.g., a guide wire, a lead wire, etc.). In some embodiments, the through-lumen can be configured to pass a fluid or agent, e.g., for delivery of the fluid or agent to a distal end of a catheter. In some embodiments, the inner diameter ID can be at least about 50 μm and up to about 5 mm, inclusive of all values and ranges therebetween.

Alternatively, in some embodiments, the magnet 210 may not have a through lumen or hole. Instead, the magnet 210 may be formed of a first material or core material with one or more layers of other material (e.g., 212, 214, 216) arranged around the core material.

In some embodiments, the inner layer 212 can be composed of a biocompatible material. In some embodiments, the inner layer 212 can be composed of platinum iridium (Pt/Ir), iron platinum (FePt), gold, stainless steel, or another biocompatible metal or metal composite. As shown, the inner layer 212 has a thickness $t_{IL}$. In some embodiments, $t_{IL}$ can be at least about 20 μm, at least about 30 μm, at least about 40 μm, at least about 50 μm, at least about 60 μm, at least about 70 μm, at least about 80 μm, at least about 90 μm, at least about 100 μm, at least about 150 μm, at least about 200 μm, at least about 250 μm, at least about 300 μm, at least about 350 μm, at least about 400 μm, at least about 450 μm, at least about 500 μm, at least about 550 μm, at least about 600 μm, at least about 650 μm, at least about 700 μm, at least about 750 μm, at least about 800 μm, at least about 850 μm, at least about 900 μm, or at least about 950 μm. In some embodiments, $t_{IL}$ can be no more than about 1 mm, no more than about 950 μm, no more than about 900 μm, no more than about 850 μm, no more than about 800 μm, no more than about 750 μm, no more than about 700 μm, no more than about 650 μm, no more than about 600 μm, no more than about 550 μm, no more than about 500 μm, no more than about 450 μm, no more than about 400 μm, no more than about 350 μm, no more than about 300 μm, no more than about 250 μm, no more than about 200 μm, no more than about 150 μm, no more than about 100 μm, no more than about 90 μm, no more than about 80 μm, no more than about 70 μm, no more than about 60 μm, no more than about 50 μm, no more than about 40 μm, or no more than about 30 μm. Combinations of the above-referenced $t_{IL}$ values are also possible (e.g., at least about 20 μm and no more than about 1 mm or at least about 50 μm and no more than about 200 μm), inclusive of all values and ranges therebetween. In some embodiments, $t_{IL}$ can be about 20 μm, about 30 μm, about 40 μm, about 50 μm, about 60 μm, about 70 μm, about 80 μm, about 90 μm, about 100 μm, about 150 μm, about 200 μm, about 250 μm, about 300 μm, about 350 μm, about 400 μm, about 450 μm, about 500 μm, about 550 μm, about 600 μm, about 650 μm, about 700 μm, about 750 μm, about 800 μm, about 850 μm, about 900 μm, about 950 μm, or about 1 mm.

In some embodiments, the magnetic layer 214 can include iron, nickel, cobalt, neodymium, boron, rare earth metals, aluminum, NdFeB, FeNb, alnico, permalloy, and any other suitable magnetic material, or combinations thereof. As shown, the magnetic layer 214 has a thickness, $t_{MM}$. In some embodiments, $t_{MM}$ can be at least about 20 μm, at least about 30 μm, at least about 40 μm, at least about 50 μm, at least about 60 μm, at least about 70 μm, at least about 80 μm, at least about 90 μm, at least about 100 μm, at least about 150 μm, at least about 200 μm, at least about 250 μm, at least about 300 μm, at least about 350 μm, at least about 400 μm, at least about 450 μm, at least about 500 μm, at least about 550 μm, at least about 600 μm, at least about 650 μm, at least about 700 μm, at least about 750 μm, at least about 800 μm, at least about 850 μm, at least about 900 μm, or at least about 950 μm. In some embodiments, $t_{MM}$ can be no more than about 1 mm, no more than about 950 μm, no more than about 900 μm, no more than about 850 μm, no more than about 800 μm, no more than about 750 μm, no more than about 700 μm, no more than about 650 μm, no more than about 600 μm, no more than about 550 μm, no more than about 500 μm, no more than about 450 μm, no more than about 400 μm, no more than about 350 μm, no more than about 300 μm, no more than about 250 μm, no more than about 200 μm, no more than about 150 μm, no more than about 100 μm, no more than about 90 μm, no more than about 80 μm, no more than about 70 μm, no more than about 60 μm, no more than about 50 μm, no more than about 40 μm, or no more than about 30 μm. Combinations of the above-referenced $t_{MM}$ values are also possible (e.g., at least about 20 μm and no more than about 1 mm or at least about 50 μm and no more than about 200 µm), inclusive of all values and ranges therebetween. In some embodiments, $t_{MM}$ can be about 20 µm, about 30 µm, about 40 µm, about 50 µm, about 60 µm, about 70 µm, about 80 µm, about 90 µm, about 100 µm, about 150 µm, about 200 µm, about 250 µm, about 300 µm, about 350 µm, about 400 µm, about 450 µm, about 500 µm, about 550 µm, about 600 µm, about 650 µm, about 700 µm, about 750 µm, about 800 µm, about 850 µm, about 900 µm, about 950 µm, or about 1 mm.

In some embodiments, the outer layer 216 can be composed of a biocompatible material. In some embodiments, the outer layer 216 can be composed of platinum iridium (PtIr), iron platinum (FePt), gold, stainless steel, or another biocompatible metal or metal composite. As shown, the outer layer 216 has a thickness $t_{OL}$. In some embodiments, $t_{OL}$ can be at least about 20 µm, at least about 30 µm, at least about 40 µm, at least about 50 µm, at least about 60 µm, at least about 70 µm, at least about 80 µm, at least about 90 µm, at least about 100 µm, at least about 150 µm, at least about 200 µm, at least about 250 µm, at least about 300 µm, at least about 350 µm, at least about 400 µm, at least about 450 µm, at least about 500 µm, at least about 550 µm, at least about 600 µm, at least about 650 µm, at least about 700 µm, at least about 750 µm, at least about 800 µm, at least about 850 µm, at least about 900 µm, or at least about 950 µm. In some embodiments, $t_{OL}$ can be no more than about 1 mm, no more than about 950 µm, no more than about 900 µm, no more than about 850 µm, no more than about 800 µm, no more than about 750 µm, no more than about 700 µm, no more than about 650 µm, no more than about 600 µm, no more than about 550 µm, no more than about 500 µm, no more than about 450 µm, no more than about 400 µm, no more than about 350 µm, no more than about 300 µm, no more than about 250 µm, no more than about 200 µm, no more than about 150 µm, no more than about 100 µm, no more than about 90 µm, no more than about 80 µm, no more than about 70 µm, no more than about 60 µm, no more than about 50 µm, no more than about 40 µm, or no more than about 30 µm. Combinations of the above-referenced $t_{OL}$ values are also possible (e.g., at least about 20 µm and no more than about 1 mm or at least about 50 µm and no more than about 200 µm), inclusive of all values and ranges therebetween. In some embodiments, $t_{OL}$ can be about 20 µm, about 30 µm, about 40 µm, about 50 µm, about 60 µm, about 70 µm, about 80 µm, about 90 µm, about 100 µm, about 150 µm, about 200 µm, about 250 µm, about 300 µm, about 350 µm, about 400 µm, about 450 µm, about 500 µm, about 550 µm, about 600 µm, about 650 µm, about 700 µm, about 750 µm, about 800 µm, about 850 µm, about 900 µm, about 950 µm, or about 1 mm. In some embodiments, the thickness $t_{MM}$ can be greater than the thicknesses $t_{IL}$ and $t_{OL}$. In some embodiments, the thicknesses $t_{IL}$ and $t_{OL}$ can be substantially the same. In some embodiments, the thicknesses $t_{IL}$ and $t_{OL}$ can be different from one another, e.g., thickness $t_{OL}$ can be greater than or less than the thickness $t_{IL}$.

As described above, the magnet 210 can be formed using DFT methods. For example, the magnet 210 can be formed from drawing together different materials (e.g., the biocompatible metal of the layers 212, 216 with the magnetizable material 214) into a DFT wire. In an example embodiment, tubes forming the layers 212, 214, 216 can be concentrically placed around a core material (e.g., a core metal) and drawn via a tube drawing process (e.g., tube sinking, rod drawing, fix plug drawing, floating plug drawing, tethered plug drawing) into a single wire. The wire can be cut to form the individual magnets 210, and the core material can be removed (e.g., by melting the core material, which can have a lower melting temperature than the material of the layers 212, 214, 216). Further details of such a process are described with reference to FIG. 4. In some embodiments, the core material can be removed (e.g., via melting) prior to cutting the wire to form the individual magnets 210. In some embodiments, the wire can be cut prior to removing the core material.

As shown, the magnet 210 includes both the inner layer 212 and the outer layer 216, which are formed of biocompatible material. In some alternative embodiments, the magnet 210 can include the outer layer 216 of biocompatible material without the inner layer 212 of biocompatible material. In such embodiments, the inner surface of the magnetizable material forming layer 214 can be disposed within a catheter or other medical device (e.g., catheter 120) or covered by a surface of the catheter to avoid direct contact of that surface with patient anatomy. Alternatively, the magnet 210 can include the inner layer 212 without the outer layer 216. In such embodiments, the outer surface of the magnetizable material forming layer 214 can be disposed within a catheter or other medical device (e.g., catheter 120) or covered by a surface of the catheter to avoid direct contact of that surface with patient anatomy. Still alternatively, the magnet 210 may not include either the inner layer 212 or the outer layer 216. In such embodiments, the magnet 210 may be formed of a magnetizable material and can be placed within a catheter or other medical device (e.g., catheter 120) such that the magnetizable material does not come into direct contact with any patient anatomy. Alternatively, the magnet 210 can be coated, after production using DFT, with biocompatible coatings, e.g., on the inner surface and/or outer surface of the magnet 210.

Figure 3A:
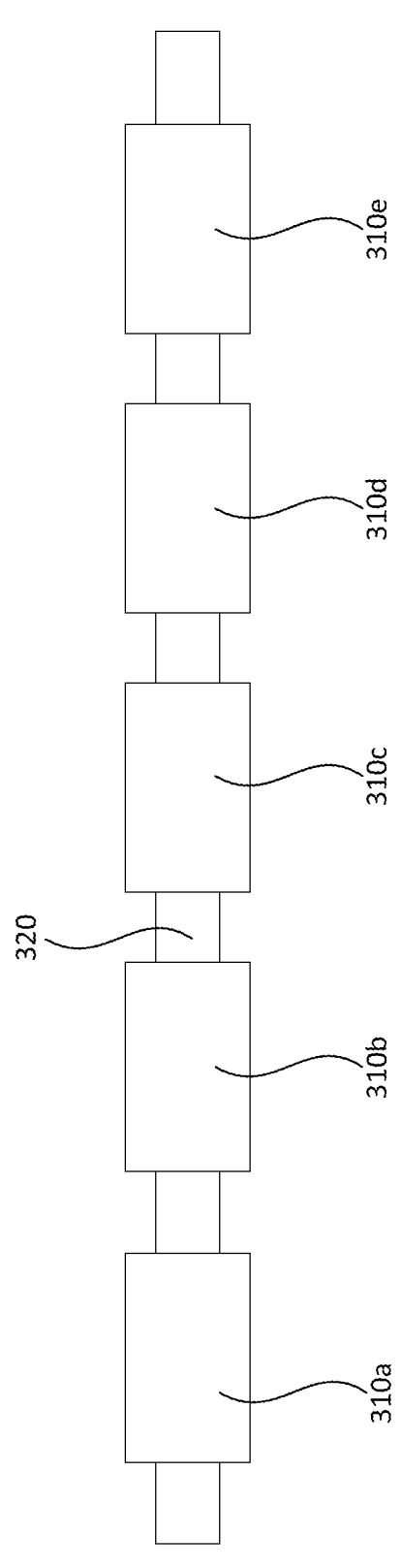
FIGS. 3A-3B are schematic illustrations of a DFT magnetic device, according to an embodiment.
Figure 3B:
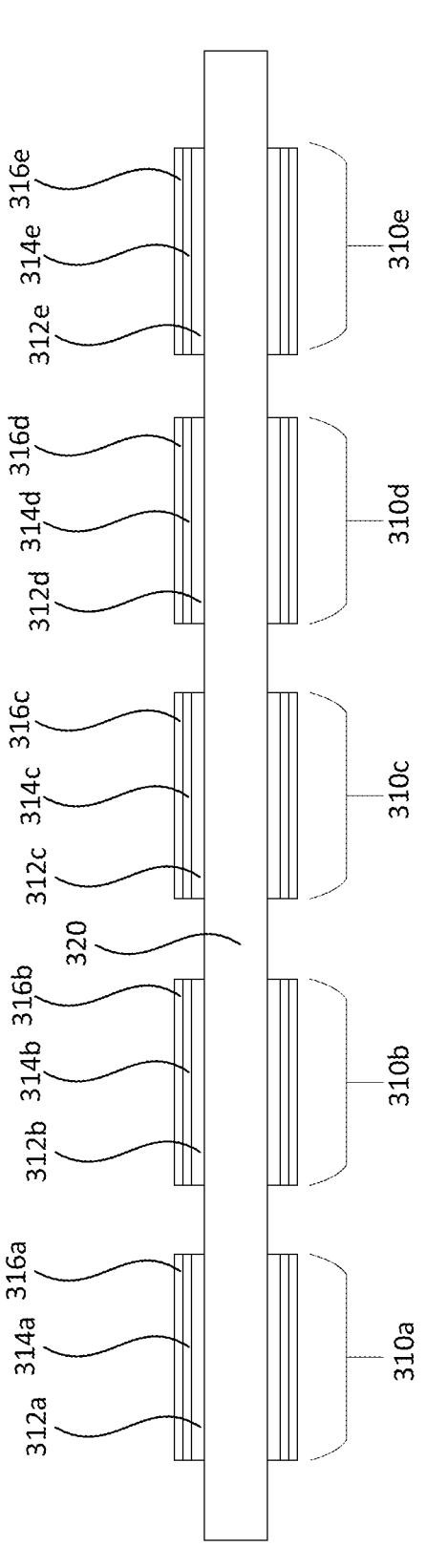

FIGS. 3A-3B are illustrations of a magnetic device 300 formed from a DFT process, according to an embodiment. As shown, the magnetic device 300 includes a plurality of magnets 310a, 310b, 310c, 310d, 310e (collectively referred to as magnets 310) disposed on a catheter 320. The magnets 310 include inner layers 312a, 312b, 312c, 312d, 312e (collectively referred to as inner layers 312), magnetic layers 314a, 314b, 314c, 314d, 314e (collectively referred to as magnetic layers 314), and outer layers 316a, 316b, 316c, 316d, 316e (collectively referred to as outer layers 316). FIG. 3A shows an exterior view of the magnetic device 300 while FIG. 3B shows a cross-sectional view of the magnetic device 300, including interior details. In some embodiments, the magnets 310, the inner layers 312, the magnetic layers 314, and the outer layers 316 can be the same or substantially similar to the magnet 210, the inner layer 212, the magnetic layer 214, and the outer layer 216, as described above with reference to FIG. 2. In some embodiments, the catheter 320 can be the same or substantially similar to the catheter 120, as described above with reference to FIG. 1. Thus, certain aspects of the magnets 310, the inner layers 312, the magnetic layers 314, the outer layers 316, and the catheter 320 are not described in greater detail herein.

In some embodiments, the catheter 320 can be a microcatheter, a guide catheter, or an ablation catheter. While the magnets 310 are described with reference to a catheter, it can be appreciated that any other type of elongate device can be used with the magnets described herein, including, for example, a wire, a sheath, an introducer, etc.

As shown, the magnet 310 includes both the inner layer 312 and the outer layer 316 of biocompatible material. In some embodiments, the magnet 310 can include the outer layer 316 of biocompatible material without the inner layer 312 of biocompatible material. In other words, the magnetic layer 314 can directly contact the catheter 320. In such embodiments, the outer surface of the catheter 320 and/or an adhesive or other material can cover the inner surface of the magnetic layer 314 such that the inner surface is not directly exposed to patient anatomy.

Figure 4:
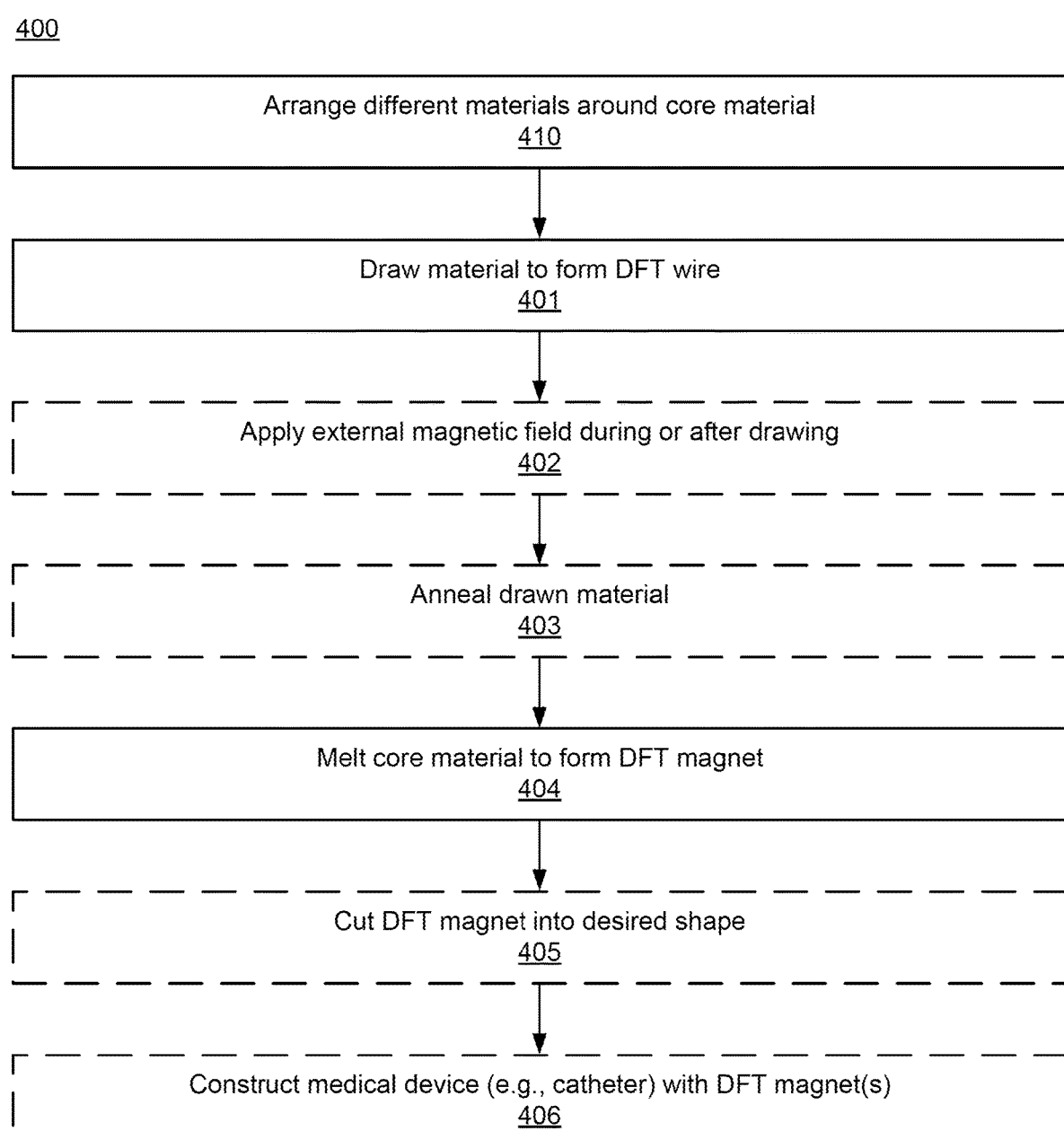
FIG. 4 shows a block diagram of a method of producing a DFT magnet, according to an embodiment.

FIG. 4 shows a block diagram of a method 400 of producing a DFT magnet, according to an embodiment. As shown, the method 400 includes arranging the different materials that form the magnet around a core material, at 410. The different materials can include one or more biocompatible materials that form the inner and/or outer layers of the magnet (e.g., inner layers 212, 312 and/or outer layers 216, 316) and one or more magnetizable or magnetic materials that form the magnetic layer of the magnet (e.g., magnetic layer 214, 314). In some embodiments, sections of biocompatible materials can be disposed around the core material, e.g., to form the inner and outer layers of the magnet and powdered magnetizable or magnetic material (e.g., granules, particles, etc. of magnetizable or magnetic material) can be placed in voids of the sections. In such embodiments, when the sections are drawn together, the different sections can form supports between the inner and outer layers of the magnet, as further described with reference to FIGS. 5A-5C below.

The method 400 includes drawing the different materials to form a DFT wire, at 401. The drawing process can include, for example, tube sinking, rod drawing, fix plug drawing, floating plug drawing, tethered plug drawing, etc. The method 400 optionally includes applying an external magnetic field during or after drawing, at 402, and/or annealing the material, at 403. The method 400 includes melting a core material of the DFT wire to form a tubular magnet, at 404. The method 400 optionally includes cutting the tubular magnet into a desired length, at 405, and/or disposing the magnet onto or integrating the magnet into a catheter or other medical device to form a magnetic device, at 406.

Describing 401-406 in detail, the method 400 includes drawing the materials or sections of materials, at 401. In some embodiments, the drawing can be through use of a die. For example, the materials or sections of materials can be drawn or pulled into a die cavity that can cause the materials to undergo plastic deformation and stretching. In some embodiments, multiple dies with successively smaller cavities can be used to produce the drawn material. In some embodiments, the different materials can be used to create a drawn multilayered, multi-material structure. The multilayered structure can include, for example, a filler or core material and one or more layers of a magnetic or magnetizable material and/or a biocompatible material. In some embodiments, the magnetic material forming the magnetic or magnetizable material can be the same or substantially similar to that of the magnetic layer 214, as described above with reference to FIGS. 2A-2C. In some embodiments, the biocompatible material forming the inner and/or outer layers of the multilayered structure can be the same or substantially similar to that of the inner layer 212 and the outer layer 216, as described above with reference to FIGS. 2A-2C.

In some embodiments, the core material can have a lower melting point than the magnetic material and the biocompatible material. In some embodiments, the core material can include silver, aluminum, etc. In some embodiments, the core material can have a melting point lower than a melting point of the magnetic material by at least about 50° C. and up to about 1,000° C., inclusive of all values and ranges therebetween.

In some embodiments, the melting point of the core material can be lower than a melting point of the biocompatible material by at least about 100° C. and up to about 1,000° C., inclusive of all values and ranges therebetween.

In some embodiments, the melting point of the core material can be less than the melting point of magnetic material, and the melting point of the magnetic material can be less than the melting point of the biocompatible material. In an example implementation, the core material can be silver, which has a melting point of 962° C.; the magnetic material can be FeNb, which has a melting point of 1370° C.; and the biocompatible material forming the inner and outer layers and optionally one or more supports can be Pt/Ir, which has a melting point of 1780° C.

At 402, the method 400 optionally includes applying an external magnetic field during or after the drawing (e.g., at least partially concurrent with 401 or after 401). In some embodiments, the magnetic field can align grains in a magnetic material, e.g., to improve magnetic performance. In some embodiments, the magnetic field can be applied to magnetize a material.

At 403, the method 400 optionally includes annealing the drawn structure. After the materials or sections of materials have been drawn, annealing can aid in removing internal stresses in the drawn materials to strengthen the structure. In some embodiments, the annealing can include cooling the patterned material at a rate of about 1° C./min to about 100° C./min, inclusive of all values and ranges therebetween.

At 404, the core material can be melted to form a magnet with a through-lumen. As the core material has a lower melting point than the biocompatible material and the magnetic material, the core material can melt, while the biocompatible material and the magnetic material remain solid. In some embodiments, the biocompatible material and the magnetic material can soften but retain their structure when the core material is melted. In some embodiments, the melting of the core material can occur in an oven, a furnace, a tube furnace, a continuously conveyed oven, or any other suitable heating device. In some embodiments, the melting of the core material can occur at a temperature of about 300° C. to about 1200° C., inclusive of all subranges and vales therebetween. During and/or after the melting of the core material, the core material can be drained from (e.g., removed from) the drawn structure to form a magnet with a through-lumen in place of the core material.

In some embodiments, the magnet formed, at 404, can be cut into several shorter magnets, at 405 (e.g., magnets having length L, as described above with reference to the magnet 210 and FIGS. 2A-2C). In some embodiments, the magnet formed, at 404, can be cut into multiple shorter magnets via laser cutting, mechanical cutting, water jet cutting, or any other suitable cutting process. The magnet can optionally be cut into a desired shape to form a magnet suitable for use in one or more medical devices. In some embodiments, patterns can be cut into the magnet to add flexibility to the magnet. A magnet cut to be flexible can curve with a catheter or other medical device (e.g., catheter 120) when placed on the catheter or medical device. In some embodiments, the cutting can include laser cutting, mechanical cutting, water jet cutting, or any other suitable cutting process. In some embodiments, the cutting can include cutting slots and/or channels into the magnet. In some embodiments, the cuts made in the magnet can include straight lines, waves or any other suitable cuts to add flexibility. In an example implementation, the cuts made in the magnet can include a tab-in-slot pattern.

In some embodiments, the method 400 can include coating the magnet, e.g., for additional protection or sealing from external elements. In some embodiments, the coating can be of a polymer such as, for example, parylene. In some embodiments, the coating can occur before the cutting at 405. In some embodiments, the coating can occur after the cutting at 405.

At 406, the magnet is optionally disposed onto or integrated into a catheter or other medical device to form a magnetic device. In some embodiments, the magnetic device can be the same or substantially similar to the magnetic devices 100 and 300, as described above with reference to FIGS. 1 and 3A-3B. Examples of medical devices with magnets formed using the DFT process, as described herein, are described below with reference to FIGS. 6A-6C.

FIGS. 5A-5C are cross-section illustrations of DFT structures (e.g., wires), according to various embodiments. The DFT structures depicted can be the drawn structure that is produced after drawing one or more sections of materials, as described with reference to FIG. 4, at 401. FIG. 5A shows a DFT wire 500a with a core material 511a, an inner layer 512a, a magnetic material 514a, and an outer layer 516a. FIG. 5B shows a DFT wire 500b with a core material 511b, an inner layer 512b, support connections 513b, a magnetic material 514b, and an outer layer 516b. FIG. 5C shows a DFT wire 500c with a core material 511c, an inner layer 512c, support connections 513c, a magnetic material 514c, and an outer layer 516c. In some embodiments, the inner layers 512a, 512b, 512c (collectively referred to as the inner layers 512), the magnetic materials 514a, 514b, 514c (collectively referred to as the magnetic materials 514), and the outer layers 516a, 516b, 516c (collectively referred to as the outer layers 516) can be the same or substantially similar to the inner layer 212, the magnetic material 214, and the outer layer 216, as described above with reference to FIGS. 2A-2C. Thus, certain aspects of the inner layers 512, the magnetic materials 514, and the outer layers 516 are not described in greater detail herein.

In some embodiments, the core materials 511a, 511b, 511c (collectively referred to as filler materials 511) can include any of the properties of the core material described above with reference to FIG. 4. For example, the core materials 511 can be selected to have a lower melting point than the biocompatible materials of the inner layers 512 or the outer layers 516 and the magnetic materials 514. In some embodiments, the filler materials 511 can be composed of silver, aluminum, etc.

FIG. 5A depicts an embodiment of a DFT wire 500a without any supports, while FIGS. 5B and 5C depict embodiments of DFT wires 500b, 500c that include supports. The support connections 513b, 513c (collectively referred to as support connections 513) can extend from the inner layers 512 to the outer layers 516 in FIGS. 5B and 5C. In some embodiments, the support connections 513 can aid in keeping the annular structure of the inner and outer layers (and the magnetic material disposed therebetween) centered around a central axis of the DFT wires 500b, 500c during the drawing process. In some embodiments, the support connections 513 can be formed from having multiple sections of materials, e.g., multiple sections bounded by biocompatible material with inner voids that can contain the magnetic material. For instance, a powdered magnetic material (or other fragmented magnetic material) can be used to produce the DFT wire. In such cases, the magnetic material can be contained within voids formed from the biocompatible material (e.g., the inner and outer layers 512, 516 as well as any side supports 513 connecting the inner and outer layers 512, 516). Without the supports 513, the various sections of materials may shift during the drawing process, thereby moving a center of the core material 511 off the centerline of the wire. As such, each section of materials can have multiple connections between the inner and outer layers 512, 516 to aid in keeping the core material 511 centered (and the inner and outer layers 512, 516 and the magnetic material 514 centered around the core material 511). When these connections are drawn during the DFT process, they can form the supports 513 as depicted in FIGS. 5B and 5C. In some embodiments, the support connections 513 can be composed of the same or substantially similar material to the biocompatible materials in the inner layers 512 and the outer layers 516. In some embodiments, the support connections 513, the inner layers 512, and/or the outer layers 516 can have a higher melting point than the core material 511 and/or the magnetic material 514 such that the support connections 513, the inner layers 512, and/or the outer layers 516 remain rigid during the melting of the core materials 511 and keep the softened magnetic material 514 from warping or becoming non-centered.

As shown, the DFT wire 500b includes 4 support connections 513b, while the DFT wire 500c includes 8 support connections 513c. In some embodiments, the DFT wire 500b or the DFT wire 500c can include between about 2 and about 100 support connections 513, inclusive of all values and ranges therebetween.

Figure 6A:
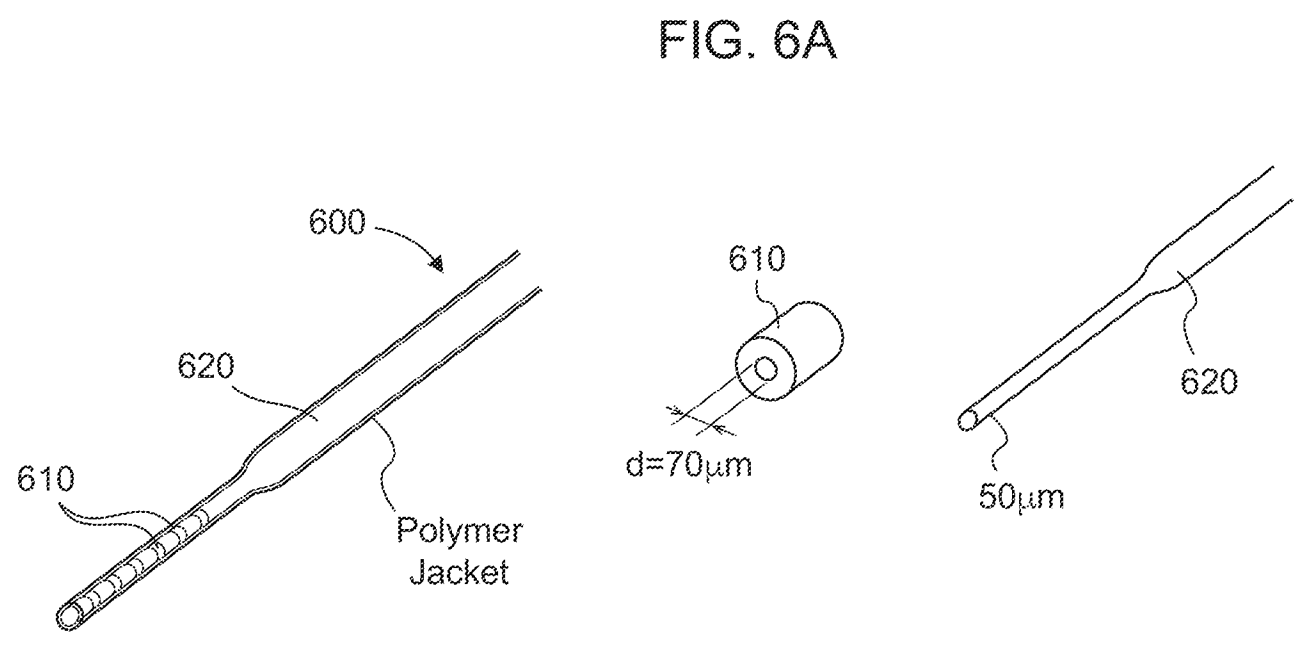
Figure 6B:
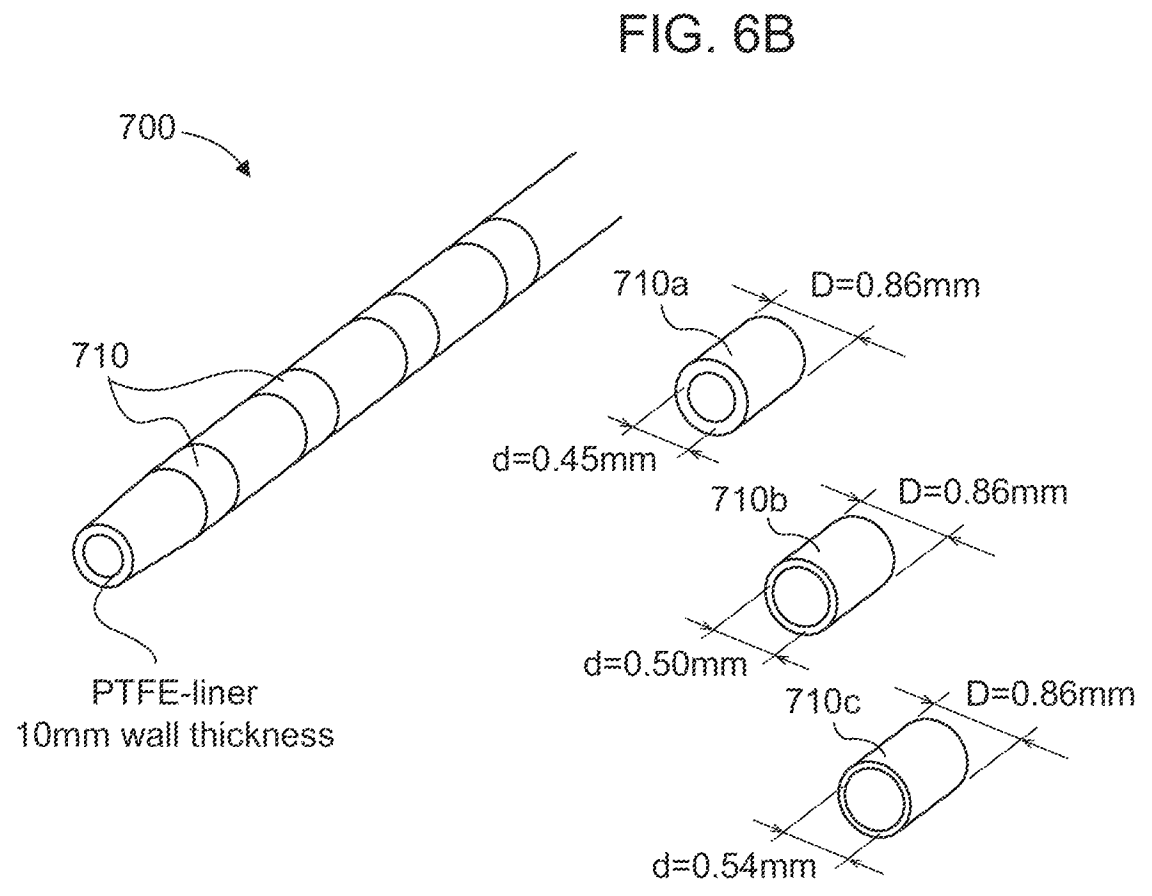
Figure 6C:
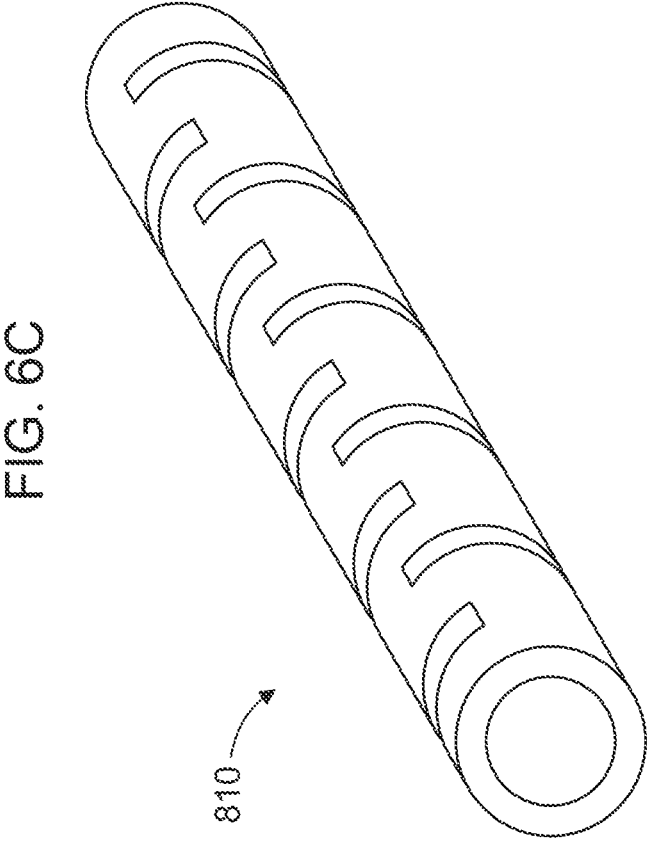

FIGS. 6A-6C illustrate example devices including DFT magnets, according to various embodiments. FIG. 6A shows a guide wire 600. As shown, the guide wire 600 can include a core wire 620 and several micromagnets 610 that are placed around a distal portion of the core wire 620. The micromagnets 610 can be structurally and/or functionally similar to other magnets described herein (e.g., magnets 110, 210, 310). The core wire 620 can be stepped such that the distal portion of the core wire is smaller in diameter than a proximal portion of the core wire. The guide wire 600 can also include a polymer jacket that is disposed over the core wire 620 and the plurality of magnets 610. The micromagnets are placed around the distal portion of the core wire 620 spaced from one another. In some embodiments, adjacent micromagnets can be spaced apart by about 1 mm to about 10 mm, inclusive of all values and ranges therebetween. The magnets 610 can have through-lumens that enable them to be placed on the distal portion of the core wire 620. As shown, each magnet 610 can have a through-lumen with a diameter of about 70 μm, and the distal portion of the core wire can have a diameter of about 50 μm. The difference between the through-lumen diameter and the core wire diameter can allow the magnets 610 to be easily slid onto the core wire 620 during construction of the guide wire 600. In some embodiments, the diameter of the through-lumen can be between about 10 μm to about 1 cm, inclusive of all values and subranges therebetween. In some embodiments, each magnet 610 can have an outer diameter that is less than or equal to an outer diameter of the proximal portion of the guide wire such that an overall outer dimension of the guide wire 600 (i.e., core wire 620 with magnets 610 and polymer jacket) does not increase in the region including the magnets 610.

FIG. 6B illustrates an example microcatheter 700. Multiple micromagnets 710a, 710b, 710c (collectively referred to as magnets 710) are disposed on different sections of the catheter 700. The micromagnets 710 can be structurally and/or functionally similar to other magnets described herein (e.g., magnets 110, 210, 310). The magnets 710 can have different diameter through-lumens, e.g., to accommodate different portions of the catheter with different core diameters. For example, portions of the catheter can be braided, coiled, or non-braided, and each of those portions can have a different diameter associated with it. As such, a first magnet 710a can have a through-lumen with a first diameter that is suitable for the non-braided portion, a second magnet 710b can have a through-lumen with a second diameter that is suitable for the coiled portion, and a third magnet 710c can have a through-lumen with a third diameter that is suitable for the braided portion. In some embodiments, the first, second, and third diameters can be different from one another, while in other embodiments, one or more of the first, second, and third diameters can be the same as another, depending on the construction of the catheter 700. In some embodiments, the first diameter can be smaller than the second and third diameters. In some embodiments, the second diameter can be smaller than the third diameter. In the example embodiment depicted, the first diameter can be about 0.45 mm, the second diameter can be about 0.50 mm, and the third diameter can be about 0.54 diameter. Each of the magnets 710 can have the same diameter (or substantially the same diameter). In the example embodiment shown, each magnet 710 has an outer diameter of about 0.86 mm. Such can ensure that an outer profile of the catheter 700 can remain substantially constant even though the inner structure (and dimensions) of the catheter 700 may change. The magnets 710 therefore allow a catheter with a smooth outer profile to be constructed. In some embodiments, the catheter 700 can include a PTFE liner and/or a polymer jacket(s) disposed adjacent to and/or over the magnets 710, e.g., to further aid in having a catheter with a smooth profile.

In some embodiments, a single tubular magnet having a longer length can be used instead of a plurality of magnets with shorter lengths. For example, FIG. 6C illustrates a tubular magnet 810 with cuts made to improve the flexibility of the magnet. The micromagnets 810 can be structurally and/or functionally similar to other magnets described herein (e.g., magnets 110, 210, 310). As shown, the cuts of the magnet 810 can include notches disposed along a length of the magnet 810. The cuts improve the flexing properties of the magnet such that the magnet can more easily curve with a catheter onto or with which the magnet has been disposed or integrated. The magnet 810 can have a through-lumen that is constant or varies in diameter along a length of the magnet 810.

Figure 7:
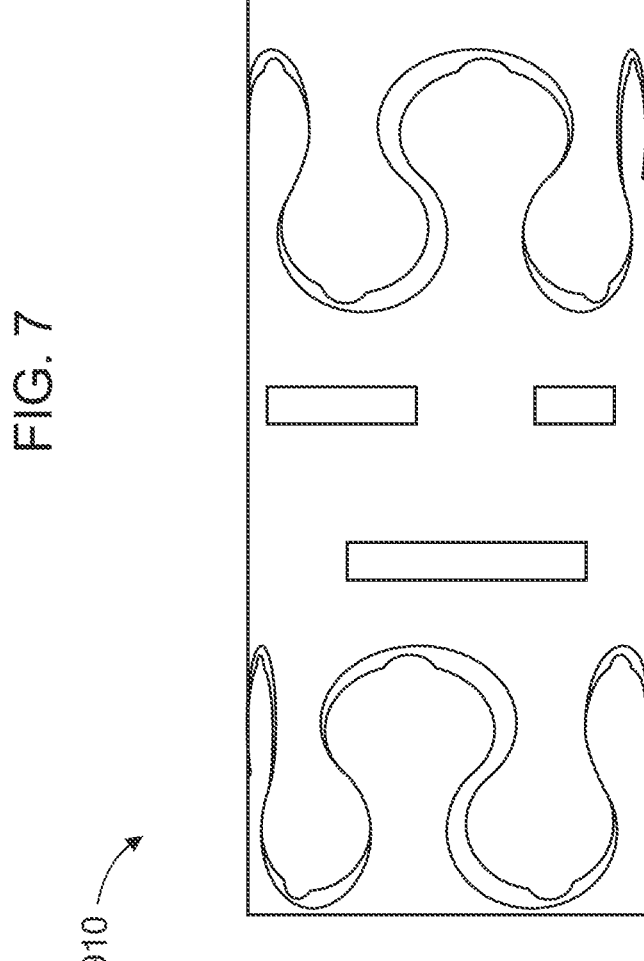
FIG. 7 shows a detailed view of a patterned cut of a DFT magnet, according to an embodiment.

FIG. 7 provides a detailed view of a magnet 910 with a pattern cut to improve flexibility. The micromagnets 910 can be structurally and/or functionally similar to other magnets described herein (e.g., magnets 110, 210, 310). As shown, the cuts of the magnet 910 include slots and wave patterns, e.g., a tub-in-slot pattern. The patterns of the cuts can be designed to reduce internal loads and stresses on the magnet during flexing and/or stretching of the magnet 910.

Figure 8:
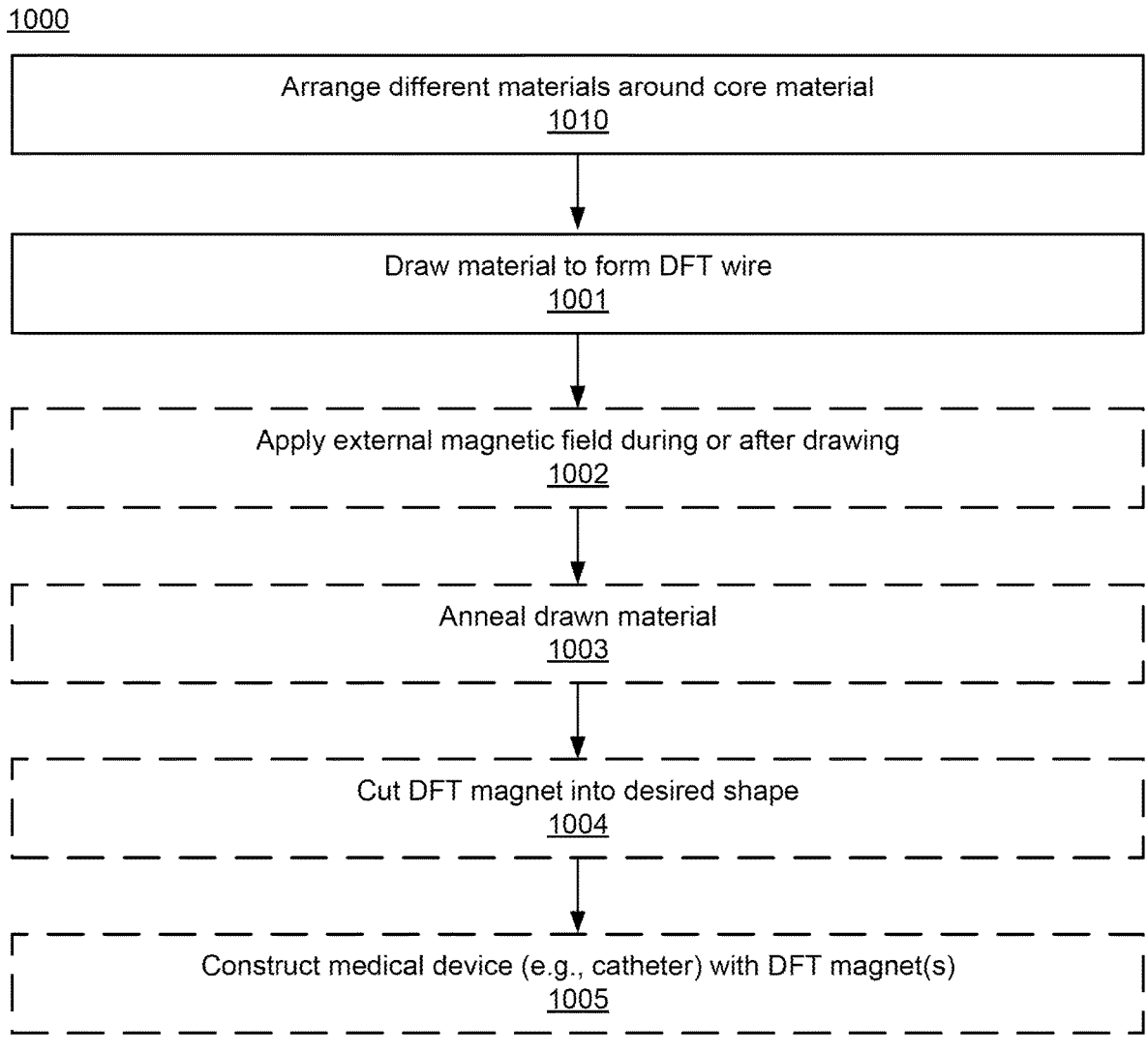
FIG. 8 shows a block diagram of a method of producing a DFT magnet, according to an embodiment.

FIG. 8 shows a block diagram of a method 1000 of producing a DFT magnet with a solid core, according to an embodiment. The method 1000 can include steps that are similar to those of method 400, but instead of forming a DFT magnet with a through hole, the method 1000 can be used to form a DFT magnet with a solid core. As shown, the method 1000 includes arranging different materials around a core material at 1010, drawing materials to form a DFT wire at 1001, and applying an external magnetic field during or after the drawing at 1002. The method 1000 can optionally include annealing the drawn material at 1003, cutting the DFT magnet into the desired shape at 1004, and constructing a medical device with the DFT magnet(s) at 1005.

The DFT wire can include a magnet or magnetic material disposed inside of an outside layer of biocompatible material or disposed between two or more layers of biocompatible material. At 1010, the different materials that form the magnet can be arranged together (e.g., with one or more outside layers of material being arranged around a core material). In some embodiments, sections of biocompatible materials can be disposed around the core material, e.g., to form the inner and outer layers of the magnet and powdered magnetizable or magnetic material (e.g., granules, particles, etc. of magnetizable or magnetic material) can be placed in voids of the sections. At 1001, the arranged materials can be drawn to form a DFT wire. The drawing process can include, for example, tube sinking, rod drawing, fix plug drawing, floating plug drawing, tethered plug drawing, etc. At 1002, an external magnetic field is optionally applied during or after drawing, forming the DFT magnet. In some embodiments, the DFT magnet can have a diameter of about 50 μm to about 1 cm, inclusive of all values and ranges therebetween.

At 1003, the drawn material is optionally annealed. At 1004, the DFT magnet is optionally cut into a desired shape. In some embodiments, the cutting can include cutting a pattern in the magnet to form a patterned magnet, the patterned magnet having increased flexibility compared to the magnet. In some embodiments, the cutting can include laser cutting. In some embodiments, 1004 can include cutting and placing at least a portion of the magnet on a microcatheter, a guide catheter, an ablation catheter, a navigation catheter and/or a therapeutic catheter such that the portion of the magnet can be used to steer the microcatheter, the guide catheter, the ablation catheter, the navigation catheter and/or the therapeutic catheter. In some embodiments, the magnet, in response to an externally applied magnetic field, is placed and/or configured such that the microcatheter, guide catheter, ablation catheter, navigation and/or therapeutic catheter can navigate through tortuous anatomy, or curve to fit within a heart chamber. At 1005, the magnet is optionally used in constructing a medical device.

As used in this specification, the singular forms "a," "an," and "the" include plural referents unless the context clearly dictates otherwise. Thus, for example, the term "a member" is intended to mean a single member or a combination of members, "a material" is intended to mean one or more materials, or a combination thereof.

The term "substantially" when used in connection with "cylindrical," "linear," and/or other geometric relationships is intended to convey that the structure so defined is nominally cylindrical, linear or the like. As one example, a portion of a support member that is described as being "substantially linear" is intended to convey that, although linearity of the portion is desirable, some non-linearity can occur in a "substantially linear" portion. Such non-linearity can result from manufacturing tolerances, or other practical considerations (such as, for example, the pressure or force applied to the support member). Thus, a geometric construction modified by the term "substantially" includes such geometric properties within a tolerance of plus or minus 5% of the stated geometric construction. For example, a "substantially linear" portion is a portion that defines an axis or center line that is within plus or minus 5% of being linear.

As used herein, the term "set" and "plurality" can refer to multiple features or a singular feature with multiple parts. For example, when referring to a set of magnets, the set of magnets can be considered as one magnet with multiple portions, or the set of magnets can be considered as multiple, distinct magnets. Additionally, for example, when referring to a plurality of electrodes, the plurality of electrodes can be considered as multiple, distinct electrodes cells or as one electrode with multiple portions. Thus, a set of portions or a plurality of portions may include multiple portions that are either continuous or discontinuous from each other. A plurality of particles or a plurality of materials can also be fabricated from multiple items that are produced separately and are later joined together (e.g., via mixing, an adhesive, or any suitable method).

Various concepts may be embodied as one or more methods, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments. Put differently, it is to be understood that such features may not necessarily be limited to a particular order of execution, but rather, any number of threads, processes, services, servers, and/or the like that may execute serially, asynchronously, concurrently, in parallel, simultaneously, synchronously, and/or the like in a manner consistent with the disclosure. As such, some of these features may be mutually contradictory, in that they cannot be simultaneously present in a single embodiment. Similarly, some features are applicable to one aspect of the innovations, and inapplicable to others.

As used herein, in particular embodiments, the terms "about" or "approximately" when preceding a numerical value indicates the value plus or minus a range of 10%. Where a range of values is provided, it is understood that each intervening value, to the tenth of the unit of the lower limit unless the context clearly dictates otherwise, between the upper and lower limit of that range and any other stated or intervening value in that stated range is encompassed within the disclosure. That the upper and lower limits of these smaller ranges can independently be included in the smaller ranges is also encompassed within the disclosure, subject to any specifically excluded limit in the stated range. Where the stated range includes one or both of the limits, ranges excluding either or both of those included limits are also included in the disclosure.

The phrase "and/or," as used herein in the specification and in the embodiments, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the embodiments, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the embodiments, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the embodiments, shall have its ordinary meaning as used in the field of patent law.

As used herein in the specification and in the embodiments, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the embodiments, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

While specific embodiments of the present disclosure have been outlined above, many alternatives, modifications, and variations will be apparent to those skilled in the art. Accordingly, the embodiments set forth herein are intended to be illustrative, not limiting. Various changes may be made without departing from the spirit and scope of the disclosure. Where methods and steps described above indicate certain events occurring in a certain order, those of ordinary skill in the art having the benefit of this disclosure would recognize that the ordering of certain steps may be modified and such modification are in accordance with the variations of the invention. Additionally, certain of the steps may be performed concurrently in a parallel process when possible, as well as performed sequentially as described above. The embodiments have been particularly shown and described, but it will be understood that various changes in form and details may be made.

The invention claimed is:

1. A method, comprising:

drawing a set of materials to form a drawn filled tubing (DFT) wire, the set of materials including a core material, a biocompatible material, and a magnetic material, the DFT wire including a core formed of the core material, first and second layers formed of the biocompatible material, and a magnetic layer formed of the magnetic material disposed between the first and second layers of biocompatible material;

applying heat to the DFT wire to melt away the core to form a magnet having the first and second layers and the magnetic layer with a through lumen, the core material having a lower melting temperature than the biocompatible material and the magnetic material; and cutting and placing at least a portion of the magnet on a microcatheter, a guide catheter, an ablation catheter, a navigation catheter and/or a therapeutic catheter such that the portion of the magnet can be used to steer the microcatheter, the guide catheter, the ablation catheter, the navigation catheter and/or the therapeutic catheter.

2. The method of claim 1, further comprising:

applying an external magnetic field to a patterned material during or after the drawing to align grains of the magnetic material.

3. The method of claim 1, wherein the DFT wire further includes one or more supports extending between the first and second layers of the biocompatible material, the one or more supports formed of the biocompatible material.

4. The method of claim 1, wherein the core material is silver or aluminum.

5. The method of claim 1, further comprising:

annealing the DFT wire.

6. The method of claim 1, further comprising:

cutting a pattern in the magnet to form a patterned magnet, the patterned magnet with increased flexibility.

7. The method of claim 6, wherein the cutting is laser cutting.

8. The method of claim 1, wherein the magnet, in response to an externally applied magnetic field, is placed and/or configured such that the microcatheter, guide catheter, ablation catheter, navigation and/or therapeutic catheter can navigate through tortuous anatomy, or curve to fit within a heart chamber.

9. The method of claim 1, wherein the through lumen of the magnet has a diameter of less than about 400 μm.

10. A method, comprising:

drawing a multilayered set of materials to form a drawn filled tubing (DFT) wire, the DFT wire including a core material, a biocompatible material disposed external to the core material, and a magnetic material disposed between layers of or adjacent to the biocompatible material;

applying a first external magnetic field during or after the drawing to align grains in the magnetic material;

applying heat to the DFT wire to melt the core material to form a magnet with a through lumen; and cutting a pattern in the magnet to form a patterned magnet, the patterned magnet configured to curve in response to a second external magnetic field.

11. The method of claim 10, wherein the DFT wire includes at least two layers of the biocompatible material.

12. The method of claim 11, wherein the DFT wire further includes one or more supports extending between the at least two layers of the biocompatible material, the one or more supports formed of the biocompatible material.

13. The method of claim 10, wherein the core material is silver or aluminum.

14. The method of claim 10, further comprising:

annealing the DFT wire.

15. The method of claim 10, wherein the through lumen of the magnet has a diameter of less than about 400 μm.

16. A method, comprising:

drawing a set of materials to form a drawn filled tubing (DFT) wire, the set of materials including a biocompatible material and a magnetic material disposed between layers of or adjacent to the biocompatible material, the DFT including at least two layers of the biocompatible material and one or more supports extending between the at least two layers of the biocompatible material, the one or more supports formed of the biocompatible material; and applying an external magnetic field during or after the drawing to align grains in the magnetic material and form a magnet.

17. The method of claim 16, further comprising:

annealing the DFT wire.

18. The method of claim 16, further comprising:

cutting a pattern in the magnet to form a patterned magnet, the patterned magnet having increased flexibility compared to the magnet.

\* \* \* \* \*